US00RE37020E

(19) United States
(12) Reissued Patent
Lin et al.

(10) Patent Number: US RE37,020 E
(45) Date of Reissued Patent: Jan. 16, 2001

(54) METHOD FOR PROVIDING NUTRITION TO ELDERLY PATIENTS

(75) Inventors: Paul M. Lin, Fullerton, CA (US); Shen-Youn Chang, Wexford, PA (US); Chris Kruzel, Boulder, CO (US)

(73) Assignee: Nestec, Ltd., Vevey (CH)

(21) Appl. No.: 09/112,575

(22) Filed: Jul. 9, 1998

Related U.S. Patent Documents

Reissue of:
(64) Patent No.: 5,589,468
Issued: Dec. 31, 1996
Appl. No.: 08/372,558
Filed: Jan. 13, 1995

(51) Int. Cl.[7] ..... A01N 43/04; A01N 45/00; A01N 43/60; A01N 43/08

(52) U.S. Cl. ..... 514/52; 514/167; 514/251; 514/458; 514/474; 514/602; 514/641; 514/702; 514/725; 514/773; 514/775; 514/776; 514/777; 514/780; 514/782; 514/904; 514/905; 426/607; 426/608

(58) Field of Search ..... 514/52, 167, 251, 514/474, 458, 602, 641, 702, 725, 773, 775, 776, 777, 780, 782, 904, 905; 426/607, 608

(56) References Cited

U.S. PATENT DOCUMENTS

| | | | | |
|---|---|---|---|---|
| 4,619,829 | * | 10/1986 | Motschan | 424/128 |
| 5,085,883 | | 2/1992 | Garleb et al. . | |
| 5,104,677 | | 4/1992 | Behr et al. . | |
| 5,221,668 | * | 6/1993 | Henningfield et al. | 514/23 |

FOREIGN PATENT DOCUMENTS

| | | | |
|---|---|---|---|
| 0614616A3 | * | 9/1994 | (EP) . |
| WO88/01861 | * | 3/1988 | (WO) . |
| WO94/27628 | * | 12/1994 | (WO) . |
| WO94/28734 | * | 12/1994 | (WO) . |

OTHER PUBLICATIONS

Sandoz Nutrition Brochure for Fibersource HN, 1992.
Sandoz Nutrition Brochure for Impact with Fiber, 1992.
Carnation NutriVent Brochure, 1991.
Clintec Enteral Product Guide for Replete and Replete with Fiber, 1992.
Recommended Dietary Allowances (National Academy Press(1989), Chapter 7, "Fat–Soluble Vitamins", pp. 78–92.
Federation of American Societies for Experimental Biology, "Physiological Effects and Health Consequences of Dietary Fiber", Jun. 1987, pp. 159–163.
Bowen et al., "Hypocarotenemia in Patients Fed Enterally with Commercial Liquid Diets", *Journal of Parenteral and Enteral Nutrition*, vol. 12, No. 5, 1988, pp. 484–489.
Abbasi et al., "Observations on the Prevalence of Protein–Calorie Undernutrition in VA Nursing Homes", *JAGS*, vol. 41, No. 2, 1993, pp. 117–121.
Abbasi et al., "Undernutrition in the Nursing Home: Prevalence, Consequences, Causes and Prevention", *Nutrition Reviews*, vol. 52, No. 4, 1994, pp. 113–122.
Anderson, "The Role of Nutrition in the Functioning of Skeletal Tissue", *Nutrition Reviews*, vol. 50, No. 12, 1992, pp. 388–394.
Berry, "Chronic Disease: How Can Nutrition Moderate the Effects?", *Nutrition Reviews*, vol. 52, No. 8, 1994, pp. S28–S30.
Blumberg, "Nutrient Requirements of the Healthy Elderly—Should There Be Specific RDAs?", *Nutrition Reviews*, vol. 52, No. 8, 1994, pp. S15–S18.
Brattström et al., "Impaired homocysteine metabolism in early–onset cerebral and peripheral occlusive arterial disease", *Atherosclerosis*, vol. 81, 1990, pp. 51–60.
Campbell, "Maintaining Hydration Status in Elderly Persons: Problems and Solutions", vol. 14, No. 3, 1992, pp. 7–10.
Chandra, "Nutritional regulation of immunity and risk of infection in old age", *Immunology*, vol. 67, 1989, pp. 141–147.
Chen et al., "Anemia and Iron Status in the Free–Living and Institutionalized Elderly in Kentucky", *Internat.J.Vit.Nutr.Res.*, vol. 59, No. 2, 1989, pp. 207–213.
Chernoff, "Meeting the Nutritional Needs of the Elderly in the Institutional Setting", *Nutrition Reviews*, vol. 52, No. 4, 1994, pp. 132–136.
Chernoff, "Physiologic Aging and Nutritional Status", *Nutrition in Clinical Practice*, vol. 5, 1990, pp. 8–13.
Chernoff, "Thirst and Fluid Requirements", *Nutrition Reviews*, vol. 52, No. 8, 1994, pp. S3–S5.
Chernoff et al., "Nutrition and Aging—Chapter 52", *Modern Nutrition in Health and Disease* published by Shills & Young, 1988, pp. 982–1000.
Codispoti et al., "Food and Nutrition For Life: Malnutrition and Older Americans", Report by the Assistant Secretary for Aging Administration on Aging, DHHS, 1994, pp. 1–45.
Corti et al., "Serum Albumin Level and Physical Disability as Predictors of Mortality in Older Persons", *JAMA*, vol. 272, No. 13, 1994, pp. 1036–1041.
Drinka et al., "Prevalence and Consequences of Vitamin Deficiency in the Nursing Home: A critical Review", *JAGS*, vol. 39, 1991, pp. 1008–1017.
Frankenfield et al., "Dietary fiber and bowel function in tube–fed patients", *Perspectives in Practice*, vol. 91, No. 5, 1991, pp. 590–599.

(List continued on next page.)

*Primary Examiner*—Nathan M. Nutter
(74) *Attorney, Agent, or Firm*—Hill & Simpson

(57) ABSTRACT

The present invention provides a method for providing nutrition to elderly patients. Pursuant to the present invention, the enteral composition includes a protein source, a lipid source, and a carbohydrate source. Preferably, the protein source includes at least 18% of the total calories. In an embodiment, the carbohydrate source includes a source of dietary fiber including a balance of soluble to insoluble fiber ratio of approximately 1:3. Still further, the composition of the present invention also includes increased levels of certain vitamins and minerals.

45 Claims, No Drawings

OTHER PUBLICATIONS

Garner, "Guide to Changing Lab Values in Elders", *Geriatric Nursing*, May/Jun. 1989, pp. 144–145.
Gaziano et al., "Dietary Beta Carotene and Decreased Cardiovascular Mortality in an Elderly Cohort", *JACC*, vol. 19, No. 3, 1992, Abstract p. 377A.
Gersovitz et al., "Human protein requirements: assessment of the adequacy of the current Recommended Dietary Allowance for dietary protein in elderly men and women", *The American Journal of Clinical Nutrition*, vol. 35, 1982, pp. 6–14.
Heymsfield et al., "Body Composition and Aging: A Study by In Vivo Neutron Activation Analysis", *American Institute of Nutrition*, 1993, pp. 432–437.
Homann et al., "Reduction in Diarrhea Incidence by Soluble Fiber in Patients Receiving Total or Supplemental Enteral Nutrition", *Journal of Parenteral and Enteral Nutrition*, vol. 18, No. 6, 1994, pp. 486–490.
Jacques et al., "Nutritional Status in Persons with and without senile cataract: blood vitamin and mineral levels", *Am.J.Clin.Nutr.*, vol. 48, 1988, pp. 152–158.
Kehayias, "Aging and Body Composition: Possibilities for Future Studies", *American Institute of Nutrition*, 1993, pp. 454–458.
Litchford et al., "Nutrient intakes and energy expenditures of residents with senile dementia of the Alzheimer's type", *Brief Communications*, vol. 87, 1987, pp. 211–213.
Manual of Clinical Dietetics, Fourth Edition, 1992, "Enteral Nutrition Support of the Elderly", pp. 333–334 and "High–Fiber Diet", pp. 411–412.
Meydani et al., "Vitamin E supplementation enhances cell–mediated immunity in healthy elderly subject", *Am.J.Clin. Nutr.*, vol. 52, 1990, pp. 557–563.
Meydani et al., "Vitamin B–6 deficiency impairs interleukin 2 production and lymphocyte proliferation in elderly adults", *Am.J.Clin.Nutr.*, vol. 53, 1991, pp. 1275–1280.
Mobarhan et al., "Nutritional Problems of the Elderly", *Clinics in Geriatric Medicine*, vol. 7, No. 2, 1991, pp. 191–214.
Morley, "Nutritional Modulation of Behavior and Immunocompetence", *Nutrition Reviews*, vol. 52, No. 8, 1994, pp. S6–S8.
Mowé et al., "Reduced nutritional status in an elderly population (>70 y) is probable before disease and possibly contributes to the development of disease", *Am.J.Clin.Nutr.*, vol. 59, 1994, pp. 317–324.
Nelson et al., "Prevalence of malnutrition in the elderly admitted to long–term–care facilities", *Journal of The American Dietetic Association*, vol. 93, No. 4, 1993, pp. 459–461.
Pinchcofsky–Devin et al., "Incidence of Protein Calorie Malnutrition int he Nursing Home Population", *Journal of the American College of Nutrition*, vol. 6, No. 2, 1987, pp. 109–112.
Prentice, "Energy expenditure in the elderly", *European Journal of Clinical Nutrition*, vol. 46, Suppl. 3, 1992, pp. S21–S28.
Rimm et al., "Vitamin E Consumption and The Risk of Coronary Heart Disease in Men", *The New England Journal of Medicine*, vol. 328, No. 20, 1993, pp. 1450–1456.
Roberts et al., "Energy Expenditure, Aging and Body Composition", *American Institute of Nutrition*, 1993, pp. 474–480.
Rolls, "Appetite and Satiety in the Elderly", *Nutrition Reviews*, vol. 52, No. 8, 1994, pp. S9–S10.
Roubenoff, "Hormones, Cytokines and Body Composition: Can Lessons from Illness be Applied to Aging?", *American Institute of Nutrition*, 1993, pp. 469–473.
Rudman et al., "Relation of Serum Albumin Concentration to Death Rate in Nursing Home Men", *Journal of Parenteral and Enteral Nutrition*, vol. 11, No. 4, 1987, pp. 360–363.
Sahyoun et al., "Dietary intakes and biochemical indicators of nutritional status in an elderly, institutionalized population", *Am.J.Clin.Nutr.*, vol. 47, 1988, pp. 524–533.
Scheppach et al., "Addition of Dietary Fiber to Liquid Formula Diets: The Pros and Cons", *Journal of Parenteral and Enternal Nutrition*, vol. 14, No. 2, 1990, pp. 204–209.
Silver et al., "Nutritional Status in an Academic Nursing Home", *JAGS*, vol. 36, No. 3, 1988, pp. 487–491.
Slavin, "Commercially Available Enteral Formulas With Fiber and Bowel Function Measures", *Nutrition In Clinical Practice*, vol. 5, 1990, pp. 247–250.
Spiegel et al., "Safety and Benefits of Fructooligosaccharides as Food Ingredients", *Food Technology*, vol. 48, No. 1, 1994, pp. 85–85.
Stafford et al., "A Study of Zinc Status of Elderly Institutionalized Patients", *Age and Ageing*, vol. 17, 1988, pp. 42–48.
Stampfer et al., "Vitamin E Consumption and The Risk of Coronary Disease in Women", *The New England Journal of Medicine*, vol. 328, No. 20, 1993, pp. 1444–1449.
Stampfer et al., "A Prospective Study of Plasma Homocyst(e)ine and Risk of Myocardial Infarction in US Physicians", *JAMA*, vol. 268, No. 7, 1992, pp. 877–881.
Steinberg, "Antioxidant Vitamins and Coronary Heart Disease", *The New England Journal of Medicine*, vol. 328, No. 20, 1993, pp. 1487–1489.
Sullivan et al., "Nutritional Support In Long–Term Care Facilities", *Nutrition In Clinical Practice*, 1987, pp. 6–13.
Thomas et al., "A Prospective Study of Outcome from Protein–Energy Malnutrition in Nursing Home Residents", *Journal of Parenteral and Enteral Nutrition*, vol. 15, No. 4, 1991, pp. 400–404.
Thurnham, "Micronutrients: how important in old age?", *European Journal of Clinical Nutrition*, vol. 46, Suppl. 3, 1992, pp. S29–S37.
Wagner, "Zinc nutriture in the elderly", *Geriatrics*, vol. 40, No. 3, 1985, pp. 111–125.
Whitehead, "COMA dietary reference values and the elderly", *European Journal of Clinical Nutrition*, vol. 46, Suppl. 3, 1992, pp. S11–S19.
Varma, "Risk for drug–induced malnutrition is unchecked in elderly patients in nursing homes", *Journal of the American Dietetic Association*, vol. 94, No. 2, 1994, pp. 192–196.
Young, "Macronutrient Needs in the Elderly", *Nutrition Reviews*, vol. 50, No. 12, 1992, pp. 454–462.
Ahmed, Effect of nutrition on the health of the elderly, Journal of the American Dietetic Association, vol. 92, No. 9, pp. 1102–1108 (1992).*
Allman et al, Pressure Sores Among Hospitalized Patients, Annals of Internal Medicine, vol. 105, pp. 337–342 (1986).*
Berkow et al, eds., The Merck Manual of Diagnosis and Therapy, Chapters 77–80, 16th Ed., pp. 933–981 (1992).*
Blumberg, Considerations of the Recommended Dietary Allowances for Older Adults, Clin Appl Nutr, vol. 1(4), pp. 9–18 (1991).*

Bowen et al, Hypocarotenemia in Patients Fed Enterally with Commercial Liquid Diets, Journal of Parenteral and Enteral Nutrition, vol. 12, No. 5, pp. 484–489 (1988).*
Bristol–Meyers Squibb Company Brochure, Introducing a new perspective in nutrition. A tube feeding that more closely simulates the normal diet, 5 pages (1990).*
Campbell et al, Increased protein requirements in elderly people; new data and retrospective reassessments, Am J Clin Nutr, vol. 60, pp. 501–509 (1994).*
Chandra, Effect of vitamin and trace–element supplementation on immune responses and infection in elderly subjects, Lancet, vol. 340, pp. 1124–1127 (1992).*
Chernoff et al, Enteral Feeding and the Geriatric Patient, Clinical Nutrition Enteral and Tube Feeding, 2nd ed., W. B. Saunders Company, Chapter 20, pp. 386–399 (1990).*
Christian et al, Vitamins, Nutrition for Living, Fourth Edition, Chapter 11, pp. 334–375 (1994).*
Diplock, The Protective Roles of Antioxidant Nutrients in Disease Prevention, Vitamin Nutrition Information Service Backgrounder, vol. 3, No. 1, pp. 1–11 (1992).*
Gaziano et al, Dietary Beta Carotene and Decreased Cardiovascular Mortality in an Elderly Cohort, American College of Cardiology: 41st Annual Scientific Session, Abstract No. 982–14 (1992).*
Heimburger et al, The Role of Protein in Nutrition, with Particular Reference to the Composition and Use of Enteral Feeding Formulas. A Consensus Report, Journal of Parenteral and Enteral Nutrition, vol. 10, No. 4, pp. 425–430 (1986).*
Henderson, Nutrition and Malnutrition in the Elderly Nursing Home Patient, Clinics in Geriatric Medicine, vol. 4, No. 3, pp. 527–547 (1988).*
Jacques et al, Nutritional status in persons with and without senile cataract: blood vitamin and mineral levels, Am J Clin Nutr, vol. 48, pp. 152–158 (1988).*
Jevity® Isotonic Liquid Nutrition With Fiber, Reach for the Standard, Ross Products Division Product Brochure, 4 pages (1994).*
Johnson et al, Preventive nutrition: Disease—specific dietary interventions for older adults, Geriatrics, vol. 47, No. 11, pp. 39–40, & 45–49 (1992).*
Joosten, Metabolic evidence that deficiencies of vitamin B–12 (cobalamin), folate, and vitamin B–6 occur commonly in elderly people, Am J Clin Nutr, vol. 58, pp. 468–476 (1993).*
Kassarjian et al, Hypochlorhydria: A Factor in Nutrition, Annu. Rev. Nutr., vol. 9, pp. 271–285 (1989).*
Kerstetter et al, Malnutrition in the institutionalized older adult, Journal of the American Dietetic Association, vol. 92, No. 9, pp. 1109–1116 (1992).*
Klein et al, Nutritional Requirements in the Elderly, Gastroenterol Clin North Am., vol. 19, No. 2, pp. 473–491 (1990).*
Litchford et al, Nutrient intakes and energy expenditures of residents with senile dementia of the Alzheimer's type, Journal of The American Dietetic Association, vol. 87, No. 2, pp. 211–213 (1987).*
McMutry et al, Mild Vitamin D Deficiency and Secondary Hyperparathyroidism in Nursing Home Patients Receiving Adequate Dietary Vitamin D, J Am Geriatr Soc., vol. 40, pp. 343–347 (1992).*
Meydani et al, Vitamin E supplementation enhances cell–mediated immunity in healthy elderly subjects, Am J Clin Nutr, vol. 52, pp. 557–563 (1990).*
Podrabsky, Nutrition in Aging, Krause's Food, Nutrition and Diet Therapy, Mahan et al ED, Chapter 14, pp. 243–225 (1992).*
Rosenberg et al, Nutritional factors in physical and cognitive functions of elderly people, Am J Clin Nutr, vol. 55, pp. 1237S–1243S (1992).*
Russell et al, Vitamin requirements of elderly people: an update, Am J Clin Nutr, vol. 58, pp. 4–14 (1993).*
Sahyoun et al, Dietary intakes and biochemical indicators of nutritional status in an elderly, institutionalized population, Am J Clin Nutr, vol. 47, pp. 524–533 (1988).*
Sandman et al, Nutritional Status and Dietary Intake in Institutionalized Patients With Alzheimer' Disease and Multiinfarct Dementia, J Am Geriatr Soc, vol. 35, pp. 31–38 (1987).*
Schlenker ED., Vitamins in the Aged, Nutrition in Aging, 2nd ed., Chapter 6, Mosby, pp. 131–145 (1993).*
Shuster et al, Ensuring Successful Home Tube Feeding in the Geriatric Population, Geriatric Nursing, vol. 15, No. 2, pp. 67–81 (1994).*
Webb et al, An evaluation of the relative contributions of exposure to sunlight and of diet to the ciculating concentrations of 25–hydroxyvitamin D in an elderly nursing home population in Boston, Am J Clin Nutr, vol. 51, pp. 1075–1081 (1990).*
Weinsler ED., Aging, Handbook of Clinical Nutrition, 2nd ed., Chapter 6, Mosby, pp. 123–127 (1989).*
Williams et al ED., Water Soluble Vitamins, Nutrition and Diet Therapy, 7th ed., Chapter 9, Mosby–Year Book Inc., pp. 199–218 (1993).*
Cezard et al, Effects of Two Protein Hydrolysates on Growth, Nitrogen Balance and Small Intestine Adaptation in Growing Rats, Biol. Neonate, vol. 65, pp. 60–67 (1994).*
Poullain et al, Dietary Whey Proteins and Their Peptides or Amino Acids: Effects of the Jejunal Muscosa of Starved Rats, Am. J. Clin. Nutr., vol. 49, pp. 71–76 (1989).*
Joosten et al, Metabolic evidence that deficiencies of vitamin B–12 (cobalamin), folate, and vitamin B–6, occur commonly in elderly people, Am J. Clin Nutr, vol. 58, p. 468 (1993).*

* cited by examiner

METHOD FOR PROVIDING NUTRITION TO ELDERLY PATIENTS

Matter enclosed in heavy brackets [ ] appears in the original patent but forms no part of this reissue specification; matter printed in italics indicates the additions made by reissue.

BACKGROUND OF THE INVENTION

The present invention relates generally to the treatment and nutritional support of patients. More specifically, the present invention relates to providing nutrition to elderly patients.

Americans greater than 65 years old were, at the turn of the century, 4% of the population; currently, they are greater than 12% of the population. Though only 12% of our population, the elderly account for greater than 40% of our acute hospital bed days, buy greater than 30% of all prescription drugs and spend 30% of our greater than 600 billion dollar health budget. Still further, it is estimated that in 2030, greater than 70 million Americans (1:5) will be over the age of 65, and the "over 85's" are expected to experience the highest percentage increase of all. The Merck manual, 16th edition, p. 2540.

As the average age of the population increases, obtaining a better understanding of the unique aspects of aging in relation to nutritional needs and treatment is imperative. Many physiologic functions decline progressively throughout adult life and have an impact on nutrition. For instance, a reduction in the number of functioning cells and the resultant slowing of metabolic processes results in a decrease in caloric requirements among the elderly. Also, the reduction in physical activity that generally accompanies aging further decreases energy requirements.

Merely decreasing the total caloric intake of an elderly patient may adversely affect the required nutrition of the patient. When the total caloric intake is reduced, the remaining food intake must carefully insure a properly balanced intake of proteins, vitamins and minerals. To reduce caloric intake in the elderly, consumption of "empty" calories (i.e. fats) must be reduced and consumption of nutrient-dense foods (i.e. carbohydrates and proteins) must be increased.

While the nutritional needs of the mature adult patient differ from adult patients, in the health care settings, standard nutritional formulas are the primary form of elemental nutrition currently being used for the elderly. Naturally, standard formulas do not take into effect the known nutritional needs of the elderly patients. These standard nutritional products must be supplemented with key micronutrients to compensate for common deficiencies and metabolic changes of the elderly patient. Moreover, since the elderly have a diminished capacity to manage a fluid load, standard formulas must be modified to produce a calorically dense formulation that will provide increased energy and nutrition with a minimum amount of fluid.

Therefore, a need exists for a nutritional formula designed to meet the nutritional needs of elderly patients.

SUMMARY OF THE INVENTION

The present invention provides a nutritional composition designed for elderly patients. More specifically, the present invention provides a method for providing nutrition to an elderly patient.

In an embodiment, the method of the present invention includes the steps of administering to the patient an effective amount of a composition including a protein source making up at least 18% of the calorie distribution of the composition; a carbohydrate source; and a lipid source including a mixture of medium and long chain triglycerides.

In an embodiment, the composition provides at least 100% of the USRDA of vitamins and minerals.

In the embodiment, the composition includes a source of dietary fiber having a soluble fiber to insoluble fiber ratio of approximately 4:1 to 1:4. Preferably, the soluble fiber constitutes approximately 30% of the dietary fiber source.

In an embodiment, the composition includes increased levels of key vitamins and minerals found to be deficient in the institutionalized elderly. Specifically, the composition includes increased levels of vitamin C, zinc, vitamin D, vitamin E, vitamin A, folic acid, vitamin $B_6$, vitamin $B_{12}$, thiamine, riboflavin, calcium and selenium.

In an embodiment, the composition further includes an omega-6 to omega-3 fatty acid ratio of approximately 4:1 to 10:1.

In another embodiment, the method of the present invention includes the step of administering to the patient an effective amount of a composition including a protein source, a carbohydrate source including a source of dietary fiber having a soluble fiber to insoluble fiber ratio of about 4:1 to 1:4 and a lipid source including a mixture of medium and long chain triglycerides.

Still further, in another embodiment, the method of the present invention includes the step of administering to the patient a therapeutically effective amount of the composition comprising a protein source, a carbohydrate source, a lipid source including a mixture of medium and long chain triglycerides, and a vitamin and mineral source including key vitamin and minerals found to be deficient in the institutionalized elderly. Specifically, the composition includes the following vitamins and minerals and their respective amounts: vitamin C containing from about 120 to 300 mg/L; zinc containing from about 15 to 30 mg/L; vitamin D containing from about 400 to 800 mg/L; vitamin E containing from about 60 to 180 mg/L; vitamin A containing from about 3000 to 6000 IU/L; folic acid containing from about 400 to 1600 $\mu$g/L; vitamin $B_6$ containing from about 2 to 8 mg/L; vitamin $B_{12}$ containing from about 6 to 8 $\mu$g/L; thiamine containing from about 1.5 to 3 mg/L; riboflavin containing from about 1.7 to 3.5 mg/L; calcium containing from about 800 to 1600 mg/L and selenium containing from about 50 to 150 $\mu$g/L.

An advantage of the present invention is that it provides a nutritional composition that is ready-to-use, nutritionally complete, and contains proteins, lipids, carbohydrates and vitamins and minerals in proportions appropriate for elderly patients.

Moreover, an advantage of the present invention is that it provides a nutritional diet for tube and oral use designed for optimal tolerance and absorption in elderly patients.

Another advantage of the present invention is that it provides a composition containing higher levels of key micronutrients to compensate for common deficiencies and metabolic changes in elderly when compared with standard formulas.

Furthermore, an advantage of the present invention is that it eliminates the need for vitamin supplementation and meets regulatory requirements of the elderly.

Yet another advantage of the present invention is that it includes an ideal fiber balance to promote good bowel function in aging patients. More specifically, the ideal fiber level of the present invention avoids constipation and prevents impaction.

Still another advantage of the present invention is that it provides a composition with increased protein levels to account for the increased needs often found in the institutionalized elderly. The composition of the present invention addresses the increased repletion requirements for protein-energy malnutrition in the older patient.

Moreover, an advantage of the present invention is that it provides a calorically dense formulation that allows for increased energy and nutrition with a minimal amount of fluid. Uniquely, the composition of the present invention meets or exceeds U.S. RDA for vitamin and minerals in one liter. As a result, the composition of the present invention is appropriate for fluid-restricted patients and is designed to accommodate slower gastric emptying, which may be seen in the elderly.

Additional features and advantages of the present invention are described in, and will be apparent from, the detailed description of the presently preferred embodiments.

DETAILED DESCRIPTION OF THE PRESENTLY PREFERRED EMBODIMENTS

Nutritional support of elderly requires prevention, recognition and treatment of nutritional depletion that may occur with aging and illness. The methods of the present invention are designed specifically to provide nutritional support to elderly patients. In this regard, the composition of the present invention is designed to meet the energy needs of an elderly patient in a reduced volume.

The protein source of the present invention provides approximately 16% to 25% of the total calories of the composition. In an embodiment, the protein source is caseinate. In an embodiment, the protein source comprises at least 18% of the total calories of the composition. Relative to calorie needs, the elderly patient needs an increased amount of protein. Therefore, the composition of the present invention includes slightly higher protein levels than standard formulas to account for increased needs often found in the institutionalized elderly.

The inventors believe that the increased protein in the composition of the present invention helps correct the protein-energy malnutrition often found in elderly patients. The higher intake of protein may correct immunologic deficiencies associated with protein depletion. Moreover, the higher intake may prevent skin breakdown, which is highly correlated with protein depletion. Still further, the higher protein level promotes more rapid restoration of body protein stores that decrease with age.

Carbohydrates provide approximately 48% to 55% of the caloric content of the composition. In an embodiment, a carbohydrate source is approximately 52% of the caloric content of the composition. Carbohydrates are an important energy source for the elderly patient as they are readily absorbed and utilized. A number of carbohydrates can be used including maltodextrin or sucrose.

In addition to simple sugars, the carbohydrate source, in an embodiment, includes a source of dietary fiber. Numerous types of dietary fiber are available. Dietary fiber passes through the small intestine undigested by enzymes and represents a kind of natural and necessary laxative. Suitable sources of dietary fiber, among others, include soy, oat or gum arabic.

The total fiber contained in the composition is approximately 8 to 15 g/L. While fiber is necessary for the elderly population since constipation is a chronic problem, the composition of the present invention contains less total fiber than other products to alleviate problems associated with impaction and the increased water requirements associated with high amounts of fiber. Some older adults may not easily tolerate large amounts of fiber without adaption. In fact, patients on narcotics or with ultramotility may be at risk for bowel obstruction, especially with the administration of excess fibers. Moreover, high fiber intake may bind calcium, reducing absorption—particularly given the high incidence of atrophic gastritis in the elderly. In a preferred embodiment, the composition includes approximately 10 g/L of total fiber.

In an embodiment, the dietary fiber is a mixture of soluble and insoluble fiber. The inventors believe that a mixture of soluble and insoluble fibers may prevent or reduce constipation and lower serum cholesterol and blood glucose in the elderly. In an embodiment, the soluble to insoluble ratio of the composition is approximately 4:1 to 1:4. In a preferred embodiment, the soluble to insoluble fiber ratio is approximately 1:3.

In the soluble/insoluble mixture, soluble fiber provides gut fuel by providing short chain free fatty acids in the large intestine. Additionally, the inventors believe that soluble fiber retains moisture. As a result thereof, while the total amount of fiber provided by the composition of the present invention is less than other standard products, the amount of soluble fiber provided is higher.

The lipid source of the present invention includes a mixture of medium chain triglycerides (MCT) and long chain triglycerides (LCT). The lipid source of the present invention is approximately 26% to about 36% of the caloric content of the composition. In an embodiment, the lipid source is approximately 30% of the caloric content of the composition.

The lipid source includes at least 20% from medium chain triglycerides. Such medium chain triglycerides are easily absorbed and metabolized in the elderly patient's body. The remainder of the lipid source is a mixture of long chain triglycerides. Suitable sources of long chain triglycerides are canola oil, corn oil, soy lecithin and residual milk fat. The lipid profile containing such long chain triglycerides is designed to have a polyunsaturated fatty acid omega-6 (n-6) to omega-3 (n-3) ratio of approximately 4:1 to 10:1. The proposed ratio of n-6:n-3 is designed to prevent suppression of the immune system caused by excessive n-6 fatty acids.

In an embodiment, the composition of the present invention includes a source of beta-carotene. Beta-carotene meets a portion of the required vitamin A, thereby meeting micronutrient requirements in a small caloric volume. It is also an important nutrient with anti-oxidant properties. For example, it may reduce or mitigate symptoms of heart disease in aging adults. Adequate amounts of beta-carotene may also protect against cataracts. The composition preferably includes approximately 2 to 10 mg/L of beta-carotene. In an embodiment, beta-carotene is present in an amount of approximately 6 mg/L.

Still further, the present invention, in an embodiment, includes a specialized vitamin and mineral profile. The composition includes at least 100% of the USRDA of all vitamins and minerals. Moreover, the composition includes higher levels of the key vitamins and minerals found to be deficient in the institutionalized elderly. Vitamin-mineral deficiencies are often associated with protein-energy malnutrition in the elderly. The increased levels of vitamins and minerals exceed U.S. RDA (for normal, healthy adults) to meet the enhanced needs of the geriatric adults. As a result, utilizing the composition of the present invention eliminates the need for vitamin and mineral supplementation.

Specifically, the composition of the present invention preferably includes increased levels of vitamin C, zinc, vitamin D, vitamin E, vitamin A, folic acid, vitamin $B_6$, vitamin $B_{12}$, thiamine, riboflavin, calcium, and selenium.

Vitamin C is preferably present in an amount of approximately 120 to 300 mg/L. Blood levels of vitamin C tend to decline with age. In fact, greater than 40% of elderly may take in less than half of the U.S. RDA for vitamin C. Even mild deficiencies may play a role in the pathogenesis of declining neurocognitive function in aging adults. Increased doses may be associated with increased immune function and exert a protective effect against cancer, heart disease and cataracts. In an embodiment, vitamin C is present in an amount of approximately 240 mg/L.

Zinc is necessary to maintain skin integrity, rate of epithelialization and collagen strength. Since intake and intestinal absorption decrease with age, low serum levels have been documented in the elderly. Supplementation with adequate zinc has been shown to restore immune function. The composition of the present invention includes from approximately 15 to 30 mg/L of zinc. In an embodiment, zinc is present in an amount of approximately 24 mg/L.

Vitamin D is necessary for adequate phosphorous absorption. Likewise, calcium absorption is impaired in the elderly and higher levels of vitamin D help with absorption and decrease hyperthyroidism. Still further, a deficiency of vitamin D caused by lack of sun exposure may be common in the institutionalized elderly. Moreover, current RDA of the vitamin may be too low for the elderly to maintain serum parathyroid hormone concentrations and healthy bone mass. The composition of the present invention includes from approximately 400 to 800 IU/L of vitamin D. In an embodiment, vitamin D is present in approximately 600 IU/L.

Vitamin E acts as an antioxidant and may protect against age-related accumulation of free-radical reactions and greater lipid peroxidation that may contribute to degeneration and disease. Supplementation with vitamin E has been shown to enhance cell-mediated immunity in the elderly. The composition of the present invention includes from approximately 60 to 180 IU/L of vitamin E. In an embodiment, vitamin E is present in an amount of approximately 100 IU/L.

The amount of vitamin A, also an antioxidant, is increased as compared with other similar formulas. Vitamin A acts as a free radical scavenger and is present in the composition in approximately 3000 to 6000 IU/L. In an embodiment, vitamin A is present in approximately 4000 IU/L.

Vitamin $B_6$ and folic acid are at increased levels because vitamin $B_6$ and folic acid absorption in the elderly is inefficient. Also, there is a high degree of deficiency of these in the elderly population. In fact, vitamin $B_6$ deficiency has been associated with neurological changes and immunocompetence in the elderly. The composition of the present invention includes from approximately 2 to 8 mg/L of vitamin $B_6$ and approximately 400 to 1600 $\mu$g/L of folic acid. In an embodiment, vitamin $B_6$ and folic acid are present in amounts of approximately 4 mg/L and 1200 $\mu$g/L, respectively.

Vitamin $B_{12}$ is at an increased level in the composition due to deficiencies in the elderly from atrophic gastritis and impaired absorption. Serum $B_{12}$ is known to decline with age. The composition of the present invention includes from approximately 6 to 18 $\mu$g/L of vitamin $B_{12}$. In an embodiment, vitamin $B_{12}$ is present in an amount of approximately 12 $\mu$g/L.

Thiamine (B) transmits impulses for central and peripheral nerve cell function. Decreased intake of thiamine may be associated with neuromuscular malfunctions and heart failure. The composition of the present invention includes from approximately 1.5 to 3 mg/L of thiamine. In an embodiment, thiamine is present in an amount of approximately 2.25 mg/L.

Adequate amounts of riboflavin ($B_2$), the level of which is also increased in the composition of the present invention, are required for proper energy and protein utilization. Deficiency of riboflavin may result in skin breakdown. The composition of the present invention includes from approximately 1.7 to 3.5 mg/L of riboflavin. In an embodiment, riboflavin is present in an amount of approximately 2.55 mg/L.

As stated above, calcium absorption is impaired in the elderly. Thus, increased levels of calcium are included in the composition of the present invention. Calcium is required for tissue repair. Moreover, calcium is important in slowing/preventing bone loss in postmenopausal osteoporosis. Increased intake may be required for adequate calcium balance. The composition of the present invention includes from approximately 800 to 1600 mg/L of calcium. In an embodiment, calcium is present in an amount of approximately 1250 mg/L.

Still further, selenium is at an increased level in the composition of the present invention. Selenium acts as an anti-oxidant and an immune stimulant. It also has some anti-inflammatory action. The composition of the present invention includes from approximately 50 to 150 mg/L of selenium. In an embodiment, selenium is present in an amount of approximately 80 $\mu$g/L.

The composition of the present invention is a ready-to-use enteral formulation. The composition can be used as a supplement or for total enteral nutritional support. The composition can be tube-fed to a patient, or fed by having the patient drink same. Preferably, the caloric density of the composition is 1.2 kcal/ml and yields a non-protein calorie-to-nitrogen ratio of 114:1 to promote positive nitrogen balance.

By way of example, and not limitation, an example of a suitable composition that may be used pursuant to the present invention is as follows:

The composition includes the following ingredients: protein: caseinate; carbohydrate: maltodextrin; fat: canola oil, corn oil, soy lecithin, and residue milk fat; dietary fiber; water; vitamin A; beta-carotene; vitamin D; vitamin E; vitamin K; vitamin C; thiamine ($B_1$); riboflavin ($B_2$); niacin; vitamin B6; folic acid; pantoth. acid; vitamin $B_{12}$; biotin; choline; taurine; carnitine; calcium; phosphorus; magnesium; zinc; iron; copper; manganese; iodine; sodium; potassium; chloride; chromium; molybdenum; and selenium.

The composition of the present invention has the following nutrient composition (per 1200 calories):

| Nutrient Composition | Amount | % U.S. RDA* |
|---|---|---|
| Protein | 54 g | 120 |
| Carbohydrate 156 | g ** | |
| Fat*** | 40.6 g | ** |

-continued

| Nutrient Composition | Amount | % U.S. RDA* |
|---|---|---|
| Dietary Fiber | 10 | ** |
| Water | 742 ml | ** |
| Vitamin A | 4000 IU | 280**** |
| Beta-Carotene | 6 mg | ** |
| Vitamin D | 600 IU | 150 |
| Vitamin E | 100 IU | 333 |
| Vitamin K | 80 mcg | ** |
| Vitamin C | 240 mg | 400 |
| Thiamine ($B_1$) | 2.25 mg | 150 |
| Riboflavin ($B_2$) | 2.55 mg | 150 |
| Niacin | 40 mg | 200 |
| Vitamin $B_6$ | 4 mg | 200 |
| Folic Acid | 1200 mcg | 300 |
| Pantoth Acid | 15 mg | 150 |
| Vitamin $B_{12}$ | 12 mcg | 200 |
| Biotin | 400 mcg | 133 |
| Choline | 452 mg | ** |
| Taurine | 100 mg | ** |
| Carnitine | 100 mg | ** |
| Calcium | 1250 mg | 125 |
| Phosphorus | 1000 mg | 100 |
| Magnesium | 400 mg | 100 |
| Zinc | 24 mg | 160 |
| Iron | 18 mg | 100 |
| Copper | 2 mg | 100 |
| Magnesium | 4 mg | ** |
| Iodine | 150 mcg | 100 |
| Sodium | 763 mg | ** |
| Potassium | 1560 mg | ** |
| Chloride | 1296 mg | ** |
| Chromium | 100 mcg | ** |
| Molybdemum | 150 mcg | ** |
| Selenium | 80 mcg | ** |

*U.S. Recommended Daily Allowance for Adults and Children 4 or More Years of Age
**U.S. RDA Not Established.
***MCT Provides 8.12 Grams
****Vitamin A Calculated As a Combination of Retinol (80% of U.S. RDA per 1000 mol) Plus Beta-Carotene. Conversion of Beta-Carotene to Retinol Occurs in the Body Up to a Maximum of 10,000 IU per 100 ml (200% of U.S. RDA).

It will be understood that various modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for providing nutrition to an elderly patient comprising administering to the patient an effective amount of a composition comprising:

a protein source including at least 18% of the calorie distribution of the composition;

a carbohydrate source; [and]

a lipid source including a mixture of medium and long chain triglycerides*; and*

*a source of dietary fiber having a soluble fiber to insoluble fiber ratio of approximately 1:4 to 4:1.*

2. The method of claim 1 wherein the composition provides at least 100% of the USRDA of vitamins and minerals in approximately 1200 calories.

[3. The method of claim 1 wherein the composition includes a source of dietary fiber having a soluble fiber to insoluble fiber ratio of approximately 1:4 to 4:1.]

4. The method of claim 1 wherein the long chain triglycerides are selected to provide a ratio of n-6 to n-3 fatty acids of about 4:1 to about 10:1.

5. The method of claim 1 wherein the composition includes a source of beta-carotene.

6. The method of claim 1 wherein the composition includes the following vitamins and minerals:

| | |
|---|---|
| Vitamin C | 120 to 300 mg/L |
| Zinc | 15 to 30 mg/L |
| Vitamin D | 400 to 800 mg/L |
| Vitamin E | 60 to 180 mg/L |
| Vitamin A | 3000 to 6000 IU/L |
| Folic acid | 400 to 1600 mg/L |
| Vitamin $B_6$ | 2 to 8 mg/L |
| Vitamin $B_{12}$ | 6 to 18 mg/L |
| Thiamine | 1.5 to 3 mg/L |
| Riboflavin | 1.7 to 3.5 mg/L |
| Calcium | 800 to 1600 mg/L |
| Selenium | 50 to 150 mg/L |

7. The method of claim 1 wherein the composition has a caloric density of approximately 1.2 kcal/ml.

8. A method for providing nutrition to an elderly patient comprising enterally administering to the patient an effective amount of a composition comprising:

a protein source;

a carbohydrate source including a source of dietary fiber having a soluble fiber to insoluble fiber ratio of about 1:4 to 4:1; and a lipid source including a mixture of medium and long chain triglycerides.

9. The method of claim 8 wherein the protein comprises at least 18% of the calorie distribution of the composition.

10. The method of claim 8 wherein the composition provides at least 100% of the USRDA of vitamins and minerals in approximately 1200 calories.

11. The method of claim 8 wherein the long chain triglycerides are selected to provide a ratio of n-6 to n-3 fatty acids of about 4:1 to about 10:1.

12. The method of claim 8 wherein the composition includes a source of beta-carotene.

13. The method of claim 8 wherein the composition includes the following vitamins and minerals:

| | |
|---|---|
| Vitamin C | 120 to 300 mg/L |
| Zinc | 15 to 30 mg/L |
| Vitamin D | 400 to 800 mg/L |
| Vitamin E | 60 to 180 mg/L |
| Vitamin A | 3000 to 6000 IU/L |
| Folic acid | 400 to 1600 mg/L |
| Vitamin $B_6$ | 2 to 8 mg/L |
| Vitamin $B_{12}$ | 6 to 18 mg/L |
| Thiamine | 1.5 to 3 mg/L |
| Riboflavin | 1.7 to 3.5 mg/L |
| Calcium | 800 to 1600 mg/L |
| Selenium | 50 to 150 mg/L |

14. The method of claim 8 wherein the composition has a caloric density of approximately 1.2 kcal/ml.

15. A method for providing nutrition to an elderly patient comprising enterally administering to the patient an effective amount of a composition comprising:

a protein source;

a carbohydrate source including approximately 8 g/L to 10 g/L of a source of dietary fiber;

a lipid source including a mixture of medium and long chain triglycerides;

a vitamin and mineral source including the following vitamins and minerals in their respective amounts:

| | |
|---|---|
| Vitamin C | 120 to 300 mg/L |
| Zinc | 15 to 30 mg/L |
| Vitamin D | 400 to 800 mg/L |
| Vitamin E | 60 to 180 mg/L |
| Vitamin A | 3000 to 6000 IU/L |
| Folic acid | 400 to 1600 mg/L |
| Vitamin $B_6$ | 2 to 8 mg/L |
| Vitamin $B_{12}$ | 6 to 18 mg/L |
| Thiamine | 1.5 to 3 mg/L |
| Riboflavin | 1.7 to 3.5 mg/L |
| Calcium | 800 to 1600 mg/L |
| Selenium | 50 to 150 mg/L |

16. The method of claim 15 wherein the protein comprises at least 18% of the calorie distribution of the composition.

17. The method of claim 15 wherein the composition includes a source of dietary fiber having a soluble fiber to insoluble fiber ratio of approximately 1:4 to 4:1.

18. The method of claim 15 wherein the long chain triglycerides are selected to provide a ratio of n-6 to n-3 fatty acids of about 4:1 to about 10:1.

19. The method of claim 15 wherein the composition has a caloric density of approximately 1.2 kcal/mL.

20. The method of claim 15 wherein the composition includes at least 100% of USRDA of vitamins and minerals.

*21. A method for providing nutrition to an elderly patient comprising enterally administering to the patient an effective amount of a composition comprising:*

*a protein source;*

*a carbohydrate source including approximately 8 g/L to 10 g/L of a source of dietary fiber;*

*a lipid source; and*

*a source of beta carotene in an amount of approximately 2 to 10 mg/L.*

*22. The method of claim 21 wherein the dietary fiber source includes a mixture of soluble and insoluble fibers.*

*23. The method of claim 21 wherein the protein source comprises at least 18% of the calorie distribution of the composition.*

*24. The method of claim 21 further comprising a vitamin and mineral source, the vitamin and mineral source providing at least 100% of the USRDA of vitamins and minerals in 1200 calories.*

*25. The method of claim 21 wherein the composition includes a source of beta-carotene.*

*26. The method of claim 25 wherein the composition includes approximately 2 to 10 mg/L of beta-carotene.*

*27. The method of claim 21 further comprising a vitamin and mineral source, the vitamin and mineral source including the following vitamins and minerals in their respective amounts:*

*Vitamin C 120 to 300 mg/L*

*Zinc 15 to 30 mg/L*

*Vitamin D 400 to 800 IU/L*

*Vitamin E 60 to 180 IU/L*

*Vitamin A 3000 to 6000 IU/L*

*Folic Acid 400 to 1600 μg/L*

*Vitamin $B_6$ 2 to 8 mg/L*

*Vitamin $B_{12}$ 6 to 18 μg/L*

*Thiamine 1.5 to 3 mg/L*

*Riboflavin 1.7 to 3.5 mg/L*

*Calcium 800 to 1600 mg/L*

*Selenium 50 to 150 mg/L.*

*28. The method of claim 21 wherein the lipid source includes a mixture of medium and long chain triglycerides, the lipid source including at least 20% medium chain triglycerides and the long chain triglycerides are selected to provide a ratio of n-6 to n-3 fatty acids of 4:1 to 10:1.*

*29. The method of claim 21 wherein the composition has a caloric density of approximately 1.2 kcal/mL.*

*30. The method of claim 21 wherein the source of dietary fiber has a soluble fiber to insoluble fiber ratio of approximately 1:4 to 4:1.*

*31. A method for providing nutrition to an elderly patient comprising enterally administering to the patient an effective amount of a composition comprising:*

*a protein source;*

*a carbohydrate source including approximately 8 g/L to 10 g/L of a source of dietary fiber; and*

*a lipid source including long chain triglycerides that are selected to provide a ratio of n-6 to n-3 fatty acids of 4:1 to 10:1.*

*32. The method of claim 31 wherein the dietary fiber source includes a mixture of soluble and insoluble fibers.*

*33. The method of claim 31 wherein the protein source comprises at least 18% of the calorie distribution of the composition.*

*34. The method of claim 31 further comprising a vitamin and mineral source, the vitamin and mineral source providing at least 100% of the USRDA of vitamins and minerals in 1200 calories.*

*35. The method of claim 31 wherein the composition includes a source of beta-carotene.*

*36. The method of claim 35 wherein the composition includes approximately 2 to 10 mg/L of beta-carotene.*

*37. The method of claim 31 further comprising a vitamin and mineral source, the vitamin and mineral source including the following vitamins and minerals in their respective amounts:*

*Vitamin C 120 to 300 mg/L*

*Zinc 15 to 30 mg/L*

*Vitamin D 400 to 800 IU/L*

*Vitamin E 60 to 180 IU/L*

*Vitamin A 3000 to 6000 IU/L*

*Folic Acid 400 to 1600 μg/L*

*Vitamin $B_6$ 2 to 8 mg/L*

*Vitamin $B_{12}$ 6 to 18 μg/L*

*Thiamine 1.5 to 3 mg/L*

*Riboflavin 1.7 to 3.5 mg/L*

*Calcium 800 to 1600 mg/L*

*Selenium 50 to 150 mg/L.*

*38. The method of claim 31 wherein the lipid source includes a mixture of medium and long chain triglycerides, the lipid source including at least 20% medium chain triglycerides.*

*39. The method of claim 31 wherein the composition has a caloric density of approximately 1.2 kcal/mL.*

*40. A method for providing nutrition to an elderly patient comprising enterally administering to the patient an effective amount of a composition comprising:*

*a protein source;*

*a carbohydrate source including approximately 8 g/L to 10 g/L of a source of dietary fiber;*

*a lipid source;*

*a source of beta-carotene; and*

*a vitamin and mineral source including the following vitamins and minerals in their respective amounts:*

*Vitamin C 120 to 300 mg/L*
*Zinc 15 to 30 mg/L*
*Vitamin D 400 to 800 IU/L*
*Vitamin E 60 to 180 IU/L*
*Vitamin A 3000 to 6000 IU/L*
*Folic Acid 400 to 1600 μg/L*
*Vitamin $B_6$ 2 to 8 mg/L*
*Vitamin $B_{12}$ 6 to 18 μg/L*
*Thiamine 1.5 to 3 mg/L*
*Riboflavin 1.7 to 3.5 mg/L*
*Calcium 800 to 1600 mg/L*
*Selenium 50 to 150 mg/L.*

*41. The method of claim 40 wherein the protein source comprises at least 18% of the calorie distribution of the composition.*

*42. The method of claim 40 wherein the composition includes approximately 2 to 10 mg/L of beta-carotene.*

*43. The method of claim 40 wherein the composition has a caloric density of approximately 1.2 kcal/mL.*

*44. The method of claim 40 wherein the lipid source includes a mixture of medium and long chain triglycerides, the lipid source including at least 20% medium chain triglycerides and the long chain triglycerides are selected to provide a ratio of n-6 to n-3 fatty acids of 4:1 to 10:1.*

*45. The method of claim 40 wherein the vitamin and mineral source provides at least 100% of the USRDA of vitamins and minerals in 1200 calories.*

*46. A method for providing nutrition to an elderly patient comprising enterally administering to the patient an effective amount of a composition comprising:*

*a protein source comprising at least 18% of the calorie distribution of the composition;*

*a carbohydrate source including approximately 8 g/L to 10 g/L of a source of dietary fiber, the source of dietary fiber including a mixture of soluble and insoluble fibers, the carbohydrate source comprising approximately 48% to 55% of the calorie distribution of the composition;*

*a lipid source comprising approximately 26% to 36% of the calorie distribution of the composition; and*

*a source of beta-carotene in an amount of approximately 2 to 10 mg/L.*

* * * * *